(12) United States Patent
Uto (10) Patent No.: US 12,390,656 B2
(45) Date of Patent: Aug. 19, 2025

(54) LIGHT THERAPY DIAGNOSTIC DEVICE AND METHOD FOR OPERATING THE SAME

(71) Applicant: KANEKA CORPORATION, Osaka (JP)

(72) Inventor: Toshihiko Uto, Settsu (JP)

(73) Assignee: KANEKA CORPORATION, Osaka (JP)

( * ) Notice: Subject to any disclaimer, the term of this patent is extended or adjusted under 35 U.S.C. 154(b) by 831 days.

(21) Appl. No.: 17/617,120

(22) PCT Filed: Jun. 2, 2020

(86) PCT No.: PCT/JP2020/021777
§ 371 (c)(1),
(2) Date: Dec. 7, 2021

(87) PCT Pub. No.: WO2020/250753
PCT Pub. Date: Dec. 17, 2020

(65) Prior Publication Data
US 2022/0226665 A1    Jul. 21, 2022

(30) Foreign Application Priority Data
Jun. 12, 2019 (JP) .................... 2019-109903

(51) Int. Cl.
*A61N 5/06* (2006.01)
*A61B 1/00* (2006.01)
*A61B 1/06* (2006.01)

(52) U.S. Cl.
CPC ........ *A61N 5/0601* (2013.01); *A61B 1/00075* (2013.01); *A61B 1/00165* (2013.01); *A61B 1/0661* (2013.01)

(58) Field of Classification Search
None
See application file for complete search history.

(56) References Cited

U.S. PATENT DOCUMENTS 3,858,577 A * 1/1975 Bass ..................... H01S 3/0007
600/176
5,231,684 A * 7/1993 Narciso, Jr. ............. G02B 6/32
385/80
(Continued)

FOREIGN PATENT DOCUMENTS

JP    2008-125939 A    6/2008
JP    2014-104138 A    6/2014

OTHER PUBLICATIONS

International Search Report, issued in PCT/JP2020/021776, dated Aug. 4, 2020.
(Continued)

*Primary Examiner* — Erica S Lee
(74) *Attorney, Agent, or Firm* — Birch, Stewart, Kolasch & Birch, LLP (57) ABSTRACT

A light therapy diagnostic device comprising a shaft, an optical waveguide disposed in a lumen of the shaft and being movable forward and backward in a longitudinal direction of the shaft, and a transparent member disposed in the lumen and located distal to the optical waveguide, wherein: the optical waveguide guides a first light and a second light; the shaft has a lateral emission window which allows the first light and the second light to be emitted toward a lateral direction and a distal emission window which allows the first light to be emitted toward a distal direction; the optical waveguide includes a core and a clad, wherein a distal end surface of the core is inclined with respect to an optical axis of the optical waveguide; the first light passes through the transparent member in a state where the optical waveguide is in contact with the transparent member.

22 Claims, 5 Drawing Sheets

(56) References Cited

U.S. PATENT DOCUMENTS

| | | | |
|---|---|---|---|
| 5,693,043 | A | 12/1997 | Kittrell et al. |
| 10,539,731 | B2* | 1/2020 | Le ............................ G02B 6/32 |
| 10,631,930 | B1* | 4/2020 | Miyagawa ............. A61B 18/24 |
| 2006/0287595 | A1* | 12/2006 | Maschke .................. A61B 8/12 604/95.01 |
| 2009/0124958 | A1* | 5/2009 | Li ........................ A61B 18/203 604/20 |
| 2010/0111118 | A1* | 5/2010 | Seo ...................... G02B 6/2804 385/28 |
| 2011/0275890 | A1 | 11/2011 | Wang et al. |
| 2016/0374562 | A1 | 12/2016 | Vertikov |
| 2017/0224420 | A1* | 8/2017 | Stringer ................. A61B 34/20 |
| 2017/0326382 | A1* | 11/2017 | Seymour .................. A61B 5/24 |
| 2017/0340898 | A1* | 11/2017 | Moor ................... A61N 5/0603 |
| 2020/0093365 | A1 | 3/2020 | Wu |
| 2020/0297970 | A1 | 9/2020 | Hamm et al. |
| 2022/0161046 | A1 | 5/2022 | Tsukamoto et al. |
| 2022/0226665 | A1 | 7/2022 | Uto |

OTHER PUBLICATIONS

International Search Report, issued in PCT/JP2020/021777, dated Aug. 11, 2020.
Written Opinion of the International Searching Authority, issued in PCT/JP2020/021776, dated Aug. 4, 2020.
Written Opinion of the International Searching Authority, issued in PCT/JP2020/021777, dated Aug. 11, 2020.

* cited by examiner

LIGHT THERAPY DIAGNOSTIC DEVICE AND METHOD FOR OPERATING THE SAME

TECHNICAL FIELD

The present invention relates to a light therapy diagnostic device used for a treatment method using light such as a photodynamic therapy (PDT) and photo-immunotherapy (PIT) and a method for operating the same.

BACKGROUND ART

Biomedical treatment methods using light such as PDT and PIT are attracting attention, and as described in the following patent literatures, optical measuring devices that are capable of emitting light for grasping a condition of a treatment site prior to the emission of the light for treatment in a living body are known.

Patent Literature 1 discloses an optical probe comprising a tubular probe outer cylinder, an optical waveguide member, a first irradiation unit, and a second irradiation unit. The optical waveguide member guides a first light and a second light disposed in an inner space of the probe outer cylinder in an axial direction of the probe outer cylinder. The first irradiation unit irradiates the first light emitted from a tip of the optical waveguide member while scanning on an irradiation target placed outside the probe outer cylinder. The second irradiation unit enables the second light emitted from the tip of the optical waveguide member to be irradiated on the irradiation target placed outside the prove outer cylinder and on a trajectory of the first light formed on the irradiation target when the first irradiation unit irradiates while scanning. When the first light and the second light are simultaneously emitted from the optical waveguide member, the first irradiation unit and the second irradiation unit irradiate the first light and the second light, respectively, to different parts on the irradiation target.

Patent Literature 2 discloses an endoscope system comprising an insertion part, an illumination light irradiation unit, a treatment light irradiation unit, a light receiving unit, and a light intensity detection unit. The insertion part is formed to have a tubular shape that can be inserted into a body cavity of a specimen. The illumination light irradiation unit is provided at a tip part of the insertion part, and is configured to irradiate illumination light for illuminating a subject in the body cavity forward of the tip part. The treatment light irradiation unit is provided integrally with or separately from the tip part, and includes a therapeutic light transmission unit that transmits therapeutic light supplied from a therapeutic light supply unit, and a light diffusing unit that diffuses and irradiates the therapeutic light transmitted by the therapeutic light transmission unit into an substantially tubular region forward of the tip part. The light receiving unit receives a return light of the illumination light emitted forward of the tip part and a return light of the therapeutic light emitted into the substantially tubular region forward of the tip part, respectively. The light intensity detection unit detects an intensity of the return light of the therapeutic light received by the light receiving unit.

CITATION LIST

Patent Literature

Patent Literature 1
   Japanese Unexamined Laid-open Patent Application Publication No. 2008-125939
Patent Literature 2
   Japanese Unexamined Laid-open Patent Application Publication No. 2014-104138

SUMMARY OF INVENTION

Technical Problem

Optical devices used in the apparatuses described in the above patent literatures are all very small in diameter, manufactured using microfabrication technologies such as MEMS, for example. Therefore, the amount of light tends to decrease both in illumination optics that illuminates a surface of a living body and in light receiving optics that receives light returned from the surface of the living body, and there is room for improvement in increasing resolution of an observation image. An object of the present invention is to provide a light therapy diagnostic device that reduces the loss due to reduction in the amount of the light used for biological observation, such as, for example, vignetting and aperture eclipse, and that improves efficiency of light utilization, and a method for operating thereof.

Solution to Problem

One embodiment of the light therapy diagnostic device of the present invention that has achieved the above object is a light therapy diagnostic device comprising: a catheter shaft having a first end and a second end in a longitudinal direction and a lumen extending in the longitudinal direction; an optical waveguide disposed in the lumen of the catheter shaft and being movable forward and backward in the longitudinal direction; and a transparent member disposed in the lumen of the catheter shaft and located distal to the optical waveguide; wherein: the optical waveguide guides a first light and a second light having a wavelength different from that of the first light; the catheter shaft has a lateral emission window located on a lateral part of the catheter shaft and a distal emission window located on a distal end part of the catheter shaft; the lateral emission window allows the first light and the second light to be emitted toward a lateral direction; the distal emission window allows the first light to be emitted toward a distal direction; the optical waveguide includes a core and a clad, wherein a normal of a distal end surface of the core is inclined with respect to an optical axis of the optical waveguide; the first light passes through the transparent member in a state where the optical waveguide is in contact with the transparent member; and the first light guided through the core is reflected at a distal end part of the optical waveguide in a state where the optical waveguide is apart from the transparent member. In the above light therapy diagnostic device, the transparent member is disposed in the lumen of the catheter shaft, the first light guided through the core is reflected at a distal end part of the optical waveguide in the state where the optical waveguide is apart from the transparent member, and the first light passes through the transparent member in the state where the optical waveguide is in contact with the transparent member, and therefore, efficiency of light utilization can be improved by reducing the loss due to reduction in the amount of the light used for biological observation while having an optical system for light therapy.

In the above light therapy diagnostic device, it is preferable that the transparent member is a short optical waveguide having a shorter optical path than the optical waveguide, and a normal of a proximal end surface of the short optical waveguide is inclined with respect to the longitudinal direction of the catheter shaft.

In the above light therapy diagnostic device, it is preferable that a proximal part of the optical waveguide is connected to a circumferential rotating member that is configured to stop rotating at a predetermined rotation angle, and a distal end surface of the optical waveguide and a proximal end surface of the short optical waveguide are parallel to each other in a state where the circumferential rotation member is at the predetermined rotation angle.

In the above light therapy diagnostic device, it is preferable that the transparent member is made of a material softer than the optical waveguide.

In the above light therapy diagnostic device, it is preferable that a distal end surface of the transparent member is perpendicular to the longitudinal direction of the catheter shaft.

In the above light therapy diagnostic device, it is preferable that the lateral emission window is disposed over an entire circumference of the catheter shaft.

In the above light therapy diagnostic device, it is preferable that a proximal part of the optical waveguide is connected to a circumferential rotating member that rotates the optical waveguide in a circumferential direction of the catheter shaft.

In the above light therapy diagnostic device, it is preferable that the optical waveguide includes a first core, a second core disposed outside the first core, and a clad disposed outside the second core, and a refractive index n1 of the first core, a refractive index n2 of the second core, and a refractive index n3 of the clad satisfy the relationship of $n1>n2>n3$.

In the above light therapy diagnostic device, it is preferable that the optical waveguide includes an intermediate clad disposed outside the first core and inside the second core, and the refractive index n1 of the first core, the refractive index n2 of the second core, and a refractive index n4 of the intermediate clad satisfy the relationship of $n1>n2>n4$.

In the above light therapy diagnostic device, it is preferable that the lateral emission window is located at a position corresponding to a non-existent area of the clad.

In the above light therapy diagnostic device, it is preferable that the second core has a light diffusion region disposed proximal to the distal end surface of the core.

In the above light therapy diagnostic device, it is preferable that surface roughness Ra of an outer surface of the second core in the light diffusion region is larger than surface roughness Ra of an outer surface of the second core in a distal region located distal to the light diffusion region, wherein the surface roughness Ra is determined based on an arithmetic average roughness Ra specified in JIS B 0601 (2001).

In the above light therapy diagnostic device, it is preferable that the second core contains light diffusing particles in the light diffusion region.

In the above light therapy diagnostic device, it is preferable that a distal end part of the catheter shaft is sharpened.

It is preferable that the above light therapy diagnostic device further comprises a light source that generates the first light, and a lens disposed between the light source and the first mirror.

In the above light therapy diagnostic device, it is preferable that the catheter shaft includes a balloon connected to the lumen thereof.

The present invention also provides a method for operating the above light therapy diagnostic device. One embodiment of a method for operating the light therapy diagnostic device of the present invention comprising the steps of: guiding the first light to the optical waveguide in a state where the core is in contact with the transparent member; guiding the first light to the optical waveguide in a state where the core is apart from the transparent member; and guiding the second light to the optical waveguide to emit the second light from the lateral emission window.

Advantageous Effects of Invention

According to the above light therapy diagnostic device and its operating method, it is possible to reduce the loss due to reduction in the amount of light used for biological observation while having an optical system for light therapy, and improve efficiency of light utilization.

DESCRIPTION OF EMBODIMENTS

Hereinafter, the present invention is specifically explained below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

One embodiment of the light therapy diagnostic device of the present invention is a light therapy diagnostic device comprising: a catheter shaft having a first end and a second end in a longitudinal direction and a lumen extending in the longitudinal direction; an optical waveguide disposed in the lumen of the catheter shaft and being movable forward and backward in the longitudinal direction; and a transparent member disposed in the lumen of the catheter shaft and located distal to the optical waveguide; wherein: the optical waveguide guides a first light and a second light having a wavelength different from that of the first light; the catheter shaft has a lateral emission window located on a lateral part of the catheter shaft and a distal emission window located on a distal end part of the catheter shaft; the lateral emission window allows the first light and the second light to be emitted toward a lateral direction; the distal emission window allows the first light to be emitted toward a distal direction; the optical waveguide includes a core and a clad, wherein a normal of a distal end surface of the core is inclined with respect to an optical axis of the optical waveguide; the first light passes through the transparent member in a state where the optical waveguide is in contact with the transparent member; and the first light guided through the core is reflected at a distal end part of the optical waveguide in a state where the optical waveguide is apart from the transparent member. In the above light therapy diagnostic device, the transparent member is disposed in the lumen of the catheter shaft, the first light guided through the core is reflected at a distal end part of the optical waveguide in the state where the optical waveguide is apart from the transparent member, and the first light passes through the transparent member in the state where the optical waveguide is in contact with the transparent member, and therefore, efficiency of light utilization can be improved by reducing the loss due to reduction in the amount of the light used for biological observation while having an optical system for light therapy.

Figure 1:
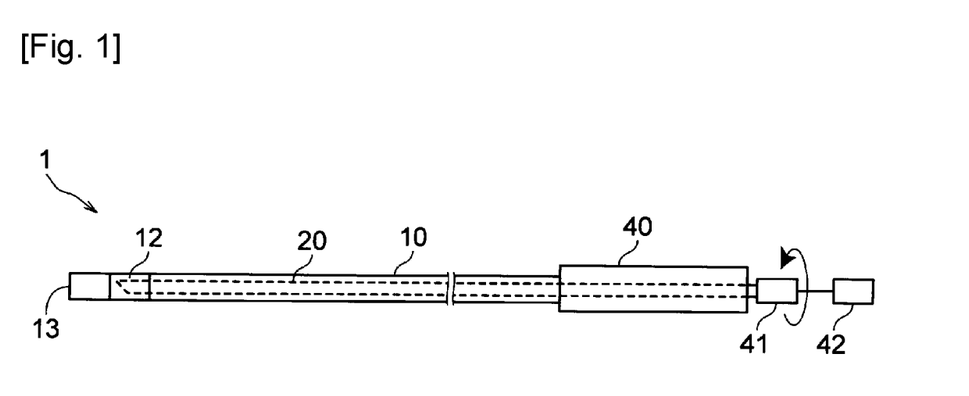
FIG. 1 shows a lateral view of a light therapy diagnostic device according to an embodiment of the present invention.
Figure 2:
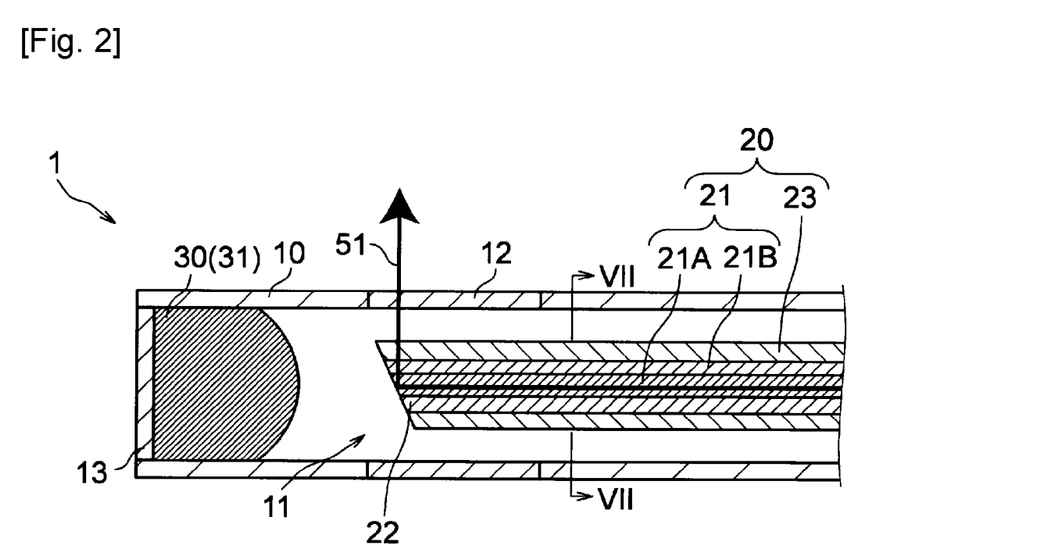
FIG. 2 shows an enlarged cross-sectional view of a distal part of the light therapy diagnostic device shown in FIG. 1, and shows a state in which a first light is emitted toward a lateral direction of the catheter shaft.
Figure 3:
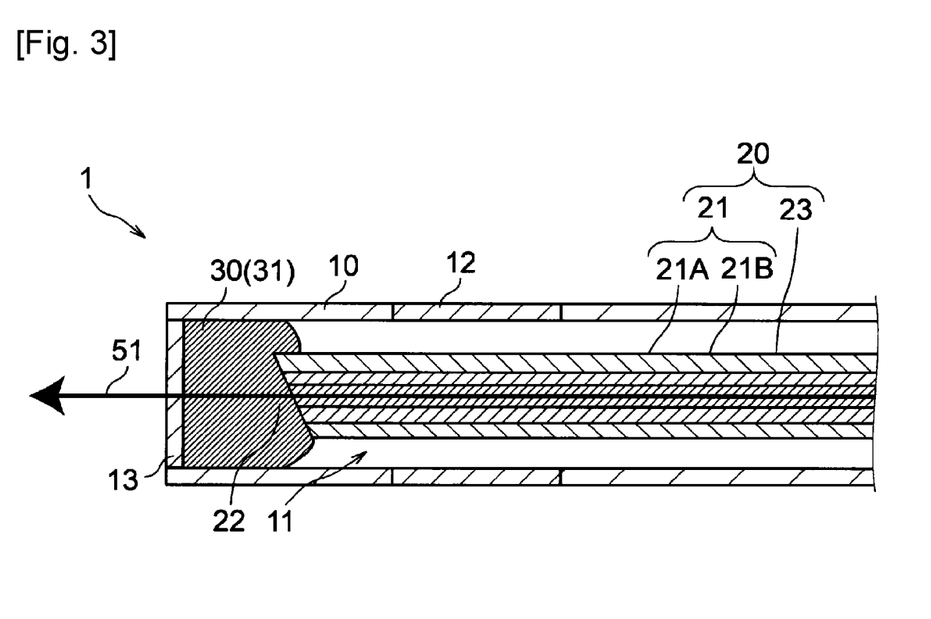
FIG. 3 shows an enlarged cross-sectional view of the distal part of the light therapy diagnostic device shown in FIG. 1, and shows a state in which a first light is emitted toward a distal direction of the catheter shaft.
Figure 4:
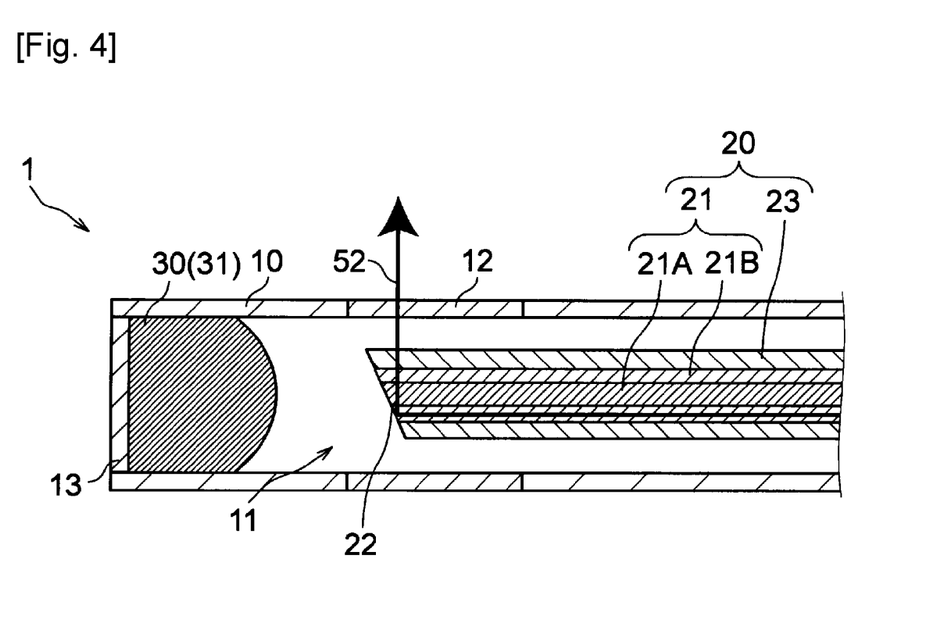
FIG. 4 shows an enlarged cross-sectional view of the distal part of the light therapy diagnostic device shown in FIG. 1, and shows a state in which a second light is emitted toward a lateral direction of the catheter shaft.

The configuration of the light therapy diagnostic device is explained with reference to FIGS. 1 to 4. FIG. 1 shows a lateral view of a light therapy diagnostic device according to an embodiment of the present invention, and FIGS. 2 to 4 show enlarged cross-sectional views of a distal part of the light therapy diagnostic device shown in FIG. 1. FIG. 2 represents a state in which a first light is emitted toward a lateral direction of the catheter shaft, FIG. 3 represents a state in which a first light is emitted toward a distal direction of the catheter shaft, and FIG. 4 represents a state in which a second light is emitted toward a lateral direction of the catheter shaft. A light therapy diagnostic device 1 comprises a catheter shaft 10, an optical waveguide 20 and a transparent member 30. Hereinafter, the light therapy diagnostic device 1 may be simply referred to as a device 1, and the catheter shaft 10 may be simply referred to as a shaft 10.

The device 1 can be used for PDT and PIT. In the device 1, an optical coherence tomography (OCT) method is preferably adopted for observing a living tissue by image diagnosis, however, an ultrasonic imaging method or a fluorescence imaging method may be adopted.

The shaft 10 has a first end and a second end that define a longitudinal direction. A distal side of the device 1 and the shaft 10 means a first end side in the longitudinal direction of the shaft 10 (in other words, a longitudinal axis direction of the shaft 10) and refers to a treatment target side. A proximal side of the light therapy diagnostic device 1 and the shaft 10 means a second end side in the longitudinal direction of the shaft 10 and refers to a hand side of a user (operator). In FIG. 1, the left side represents the distal side, and the right side represents the proximal side. Further, in a radial direction of the shaft 10, an inner side means a direction toward a center of the longitudinal axis of the shaft 10, and an outer side means a direction opposite to the inner side, namely a radiation direction.

The shaft 10 has a lumen 11 extending in the longitudinal direction. The shaft 10 has a tubular structure to dispose an optical waveguide 20 in the lumen 11. Since the shaft 10 is inserted into a body, it preferably has flexibility. Examples of the tubular structure of the shaft 10 include: a hollow body formed by arranging one or a plurality of wires in a certain pattern; the hollow body of which at least one of an inner surface and an outer surface thereof is coated with a resin; a cylindrical resin tube; and combination thereof (for example, those connected in the longitudinal direction of the shaft 10). As the hollow body in which wires are arranged in a certain pattern, a tubular body having a mesh structure by which wires are simply crossed or knitted, or a coil in which a wire is wound is exemplified. The wire may be one or a plurality of single wires, or may be one or a plurality of stranded wires. The resin tube can be manufactured, for example, by extrusion molding. In the case where the shaft 10 is made of a tubular resin tube, the shaft 10 can be composed of a single layer or a plurality of layers. A part of the shaft 10 in the longitudinal direction or a circumferential direction may be composed of a single layer, and another part of that may be composed of a plurality of layers. As shown in FIG. 1, a handle 40 gripped by an operator is preferably connected to a proximal part of the shaft 10. The device 1 may be incorporated in an endoscope or may be used as a combined device. This enables more detailed observation and treatment of a target site.

The shaft 10 can be composed of, for example, a synthetic resin such as a polyolefin resin (for example, polyethylene, polypropylene), a polyamide resin (for example, nylon), a polyester resin (for example, PET), an aromatic polyetherketone resin (for example, PEEK), a polyether polyamide resin, a polyurethane resin, a polyimide resin and a fluororesin (for example, PTFE, PFA, ETFE), or a metal such as stainless steel, carbon steel and nickel-titanium alloy. These may be used alone or in combination of two or more.

The optical waveguide 20 is disposed in the lumen 11 of the shaft 10 and can move forward and backward in the longitudinal direction of the shaft 10. The optical waveguide 20 guides a first light 51 and a second light 52 having a wavelength different from that of the first light 51. Since the optical waveguide 20 is disposed so as to be movable forward and backward in the longitudinal direction of the shaft 10, it is possible to switch between contact and non-contact between the optical waveguide 20 and the transparent member 30. The optical waveguide 20 has a core 21 and a clad 23, and a normal of a distal end surface 22 of the core 21 is inclined with respect to an optical axis of the optical waveguide 20. Examples of the optical waveguide 20 include an optical fiber. A light source is preferably connected to a proximal part of the optical waveguide 20. Thereby, the first light 51 and the second light 52 can enter the optical waveguide 20.

By moving the optical waveguide 20 in the lumen 11 of the shaft 10 in the longitudinal direction of the shaft 10, a position of the optical waveguide 20 relative to the shaft 10 can be changed. Thereby, a user can switch between a lateral observation mode, in which a lateral side of the device 1 is observed by emitting the first light 51 from a lateral emission window 12, and a forward observation mode, in which a front of the device 1 is observed by emitting the first light 51 from a distal emission window 13. A risk of the device 1 puncturing a blood vessel can be reduced when puncturing the device 1 into a body by switching it to the forward observation mode. After inserting the device 1 to a predetermined position, a target site can be observed by switching it to the lateral observation mode.

It is preferable that the first light 51 is an observation light for grasping a condition of a treatment site or its surrounding site, and the second light 52 is a treatment light. Thereby, both grasping a condition of a treatment site and providing treatment with one device 1 can be conducted, and it is possible to perform diagnosis and treatment at the same time, which has been difficult in the past. By observing a target site with the observation light after irradiation of the treatment light, a result of treatment of the target site can be confirmed. As a result, procedure time and treatment period can be shortened.

For the observation of a living tissue by OCT, the first light 51 is preferably near-infrared light, and more preferably infrared light. As a result, passability of the first light 51 to the living tissue is increased. The light source of the first light 51 may be a super luminescent diode light source, a super continuum light source, or a wavelength sweep laser. The wavelength (center wavelength) of the first light 51 may be, for example, 1.3 µm or longer, 1.35 µm or longer, or 1.4 µm or longer, and may also be allowable to be 1.8 µm or shorter, 1.75 µm or shorter, or 1.7 µm or shorter.

The second light 52 is preferably a laser beam which irradiates a living tissue and has a wavelength suitable for phototherapy such as PDT and PIT. The wavelength of the second light 52 is preferably shorter than the wavelength of the first light 51. The wavelength of the second light 52 may be, for example, 0.64 µm or longer, 0.65 µm or longer, or 0.66 µm or longer, and may also be allowable to be 0.72 µm or shorter, 0.71 µm or shorter, or 0.7 µm or shorter.

The first light 51 and the second light 52 may be emitted from one light source, or the first light 51 and the second light 52 may be emitted from different light sources from each other.

It is preferable that the device 1 comprises a light source 42 that generates the first light 51 and a lens (not shown) disposed between the light source 42 and a distal end surface 22 of the core 21. The first light 51 can enter the optical waveguide 20 by the light source 42 and the lens focuses the first light 51, whereby it is possible to obtain an image of a living tissue on a lateral side of the lateral emission window 12 or an image of a living tissue on a distal side of the distal emission window 13. The lens may be located proximal to the optical waveguide 20, may be located in the optical waveguide 20, or may be located distal to the optical waveguide 20. As the lens, a so-called GRIN lens, which is composed of a continuously changing refractive index, is preferably used.

The shaft 10 has the lateral emission window 12 located on a lateral part of the shaft 10 and the distal emission window 13 located on a distal end part of the shaft 10. The lateral emission window 12 allows the first light 51 and the second light 52 to be emitted toward a lateral direction therefrom, and the distal emission window 13 allows the first light 51 to be emitted toward a distal direction therefrom. By providing the emission windows on the shaft 10 in this manner, the lights can be emitted from the emission windows.

The lateral emission window 12 is preferably formed on a sidewall of the shaft 10. The lateral emission window 12 is preferably disposed so as to extend in a circumferential direction of the shaft 10, and more preferably disposed over an entire circumference of the shaft 10. Thereby, the second light 52 can be emitted over a wide area at once, so that a burden on a patient can be reduced.

The lateral emission window 12 is preferably located proximal to a distal end of the shaft 10. A proximal end of the lateral emission window 12 can be placed, for example, within 10 cm from the distal end of the shaft 10.

The distal emission window 13 is preferably formed on a distal end surface of the shaft 10. This makes it easier to emit the first light 51 toward a distal direction from the distal emission window 13. The distal end surface of the shaft 10 may be a flat surface or a curved surface. As a result, the distal emission window 13 can also be formed in a flat surface or a curved surface.

The lateral emission window 12 and the distal emission window 13 may be made of a material that transmits the first light 51 or the second light 52. It is preferable that a constituent material of the lateral emission window 12 and the distal emission window 13 has a higher transmittance than a constituent material of a part of the shaft 10 where the emission window is not formed. Regarding the material constituting the lateral emission window 12 and the distal emission window 13, the description of the constituent materials of the shaft 10 and the below-described transparent material 30 can be referred to. The material constituting the lateral emission window 12 and the distal emission window 13 may be the same or different from each other.

As shown in FIG. 2, the transparent member 30 is disposed in the lumen 11 of the shaft 10 and is located distal to the optical waveguide 20. A normal of the distal end surface 22 of the core 21 of the optical waveguide 20 is inclined with respect to the optical axis of the optical waveguide 20. Therefore, as shown in FIG. 2, in the state where the optical waveguide 20 is apart from the transparent member 30, the first light 51 guided through the core 21 is reflected at a distal end part of the optical waveguide 20. As a result, the first light 51 can be emitted from the side emission window 12 toward a lateral direction, and so it becomes possible to grasp a condition of a living tissue on a lateral side of the shaft 10. In OCT, a tomographic image is created based on the reflected light when the first light 51 is irradiated to a living tissue. In detail, the reflection of the first light 51 at the distal end part of the optical waveguide 20 is caused by difference between a refractive index of the core 21 of the optical waveguide 20 and a refractive index of the air present in the lumen 11 of the shaft 10. For example, when the refractive index of the core 21 is set to 1.45, $\sin \theta c = 1/1.45 = 0.6896$ according to Snell's law is derived, since the refractive index of air is about 1, and so the critical incident angle $\theta c$ comes to be about 43.6°. Therefore, by making the angle between the normal of the distal end surface 22 of the core 21 and the optical axis of the optical waveguide 20 larger than 43.6°, the first light 51 incident on the reflection interface from the core 21 side can be emitted toward a lateral direction through the lateral emission window 12. The above refractive index indicates are values for light of wavelength 589.3 nm (D ray of sodium).

Meanwhile, as shown in FIG. 3, in the case where the optical waveguide 20 is in contact with the transparent member 30, the first light 51 transmits through the transparent member 30. As a result, the first light 51 can be emitted toward the distal direction from the distant emission window 13, and so it becomes possible to grasp a condition of a living tissue on a distal side of the device 1. In detail, it is preferable to set the refractive indexes of the core 21 of the optical waveguide 20 and the transparent member 30 to the same value or close to each other. Since reflection does not occur at the interface between the core 21 and the transparent member 30 when the core 21 and the transparent member 30 are in contact with each other, the first light 51 incident from the core 21 side passes through the transparent member 30. As a result, the first light 51 can be emitted in the distal direction of the shaft 10.

By making the optical waveguide 20 and the transparent member 30 contact or non-contact as described above, the emission direction of the first light 51 can be easily switched between the lateral direction and the distal direction. Therefore, according to the device 1, efficiency of light utilization can be improved by reducing the loss due to reduction in the amount of the light used for biological observation while having an optical system for light therapy.

As shown in FIG. 4, in the state where the optical waveguide 20 is apart from the transparent member 30, the second light 52 guided through the core 21 is preferably reflected at a distal end part of the optical waveguide 20. As a result, the second light 52 can be emitted in the lateral direction from the side emission window 12. By irradiating the second light 52 to a living tissue on a lateral side of the shaft 10, treatment of living using the light can be performed.

The distal end surface 22 of the core 21 is preferably a flat surface. Thereby, in the state where the optical waveguide 20 is apart from the transparent member 30, the first light 51 guided through the core 21 is easily reflected on the distal end surface 22 of the core 21.

The inclination angle of the normal of the distal end surface 22 of the core 21 with respect to the optical axis of the optical waveguide 20 can be appropriately set in relation with the refractive indexes of the core 21 of the optical waveguide 20 and the transparent member 30. The inclination angle may be, for example, 40 degrees or larger, 41 degrees or larger, or 42 degrees or larger, and may also be allowable to be 47 degrees or smaller, 46 degrees or smaller, or 45 degrees or smaller.

The refractive index of the core 21 of the optical waveguide 20 may be larger than the refractive index of the clad 23, and may be, for example, 1.4 or more, 1.41 or more, 1.43 or more, or 1.45 or more, and may also be allowable to be 1.7 or less, 1.6 or less, or 1.5 or less.

The transparent member 30 may be made of a material which the first light 51 is capable of transmitting. It is preferable that the refractive indexes of the core 21 of the optical waveguide 20 and the transparent member 30 are the same or close to each other. Thereby, in the state where the core 21 of the optical waveguide 20 is in contact with the transparent member 30, the first light 51 can be reliably emitted in the distal direction. Therefore, the refractive index of the transparent member 30 is preferably 1.4 or more, more preferably 1.41 or more, even more preferably 1.43 or more, still even more preferably 1.45 or more, and may be also allowable to be 1.7 or less, 1.6 or less, or 1.5 or less.

The transparent material 30 may be made of a material which the first light 51 transmits. The transparent member 30 can be made of a synthetic resin such as (meth)acrylic resin (for example, polymethylmethacrylate (PMMA)), polycarbonate resin (for example, polydiethylene glycol bisallyl carbonate (PC)), polystyrene resin (for example, methyl methacrylate/styrene copolymer resin (MS), acrylonitrile styrene resin (SAN)), polyamide resin (for example, nylon), and polyolefin resin. These may be used alone or in combination of two or more.

As shown in FIGS. 2 to 4, the transparent member 30 is preferably a resin lump 31. This makes it easier to place the transparent member 30 inside the shaft 10. The resin lump 31 preferably closes the lumen 11 of the shaft 10. Thereby, a contact area is secured when the optical waveguide 20 and the resin lump 31 come into contact.

It is preferable that the transparent member 30 is made of a material softer than the optical waveguide 20. When the optical waveguide 20 and the transparent member 30 come into contact, the transparent member 30 can easily adhere to the optical waveguide 20, thereby facilitating irradiation of the first light 51 in the distal direction.

It is preferable that a distal end surface of the transparent member 30 is perpendicular to the longitudinal direction of the shaft 10. Thereby, reflection loss of the first light 51 at the distal end surface of the transparent member 30 is suppressed, and the first light 51 is easily emitted in the distal direction.

Figure 5:
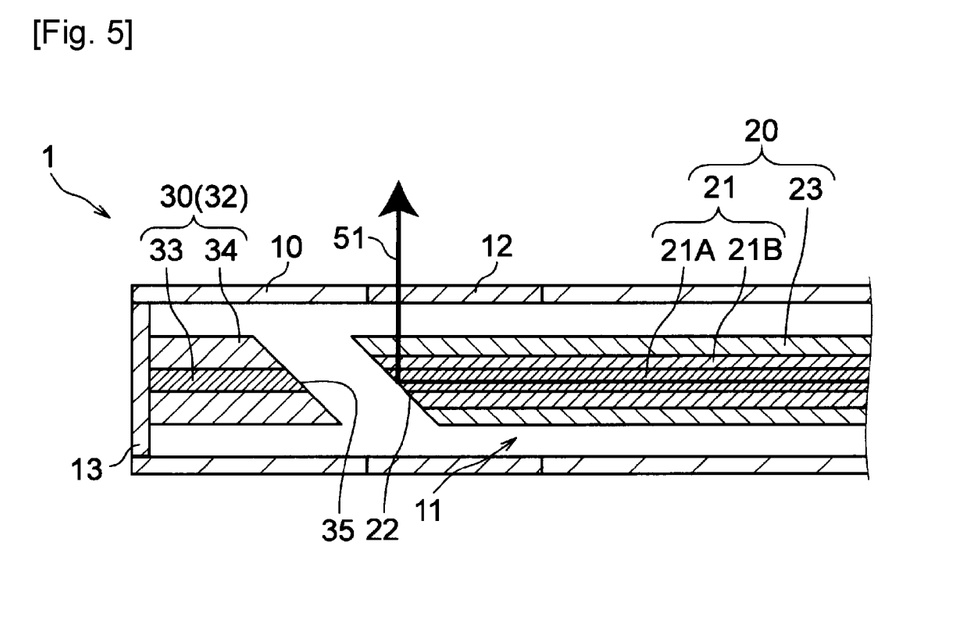
FIG. 5 shows a cross-sectional view of a modified example of the light therapy diagnostic device of FIG. 2.
Figure 6:
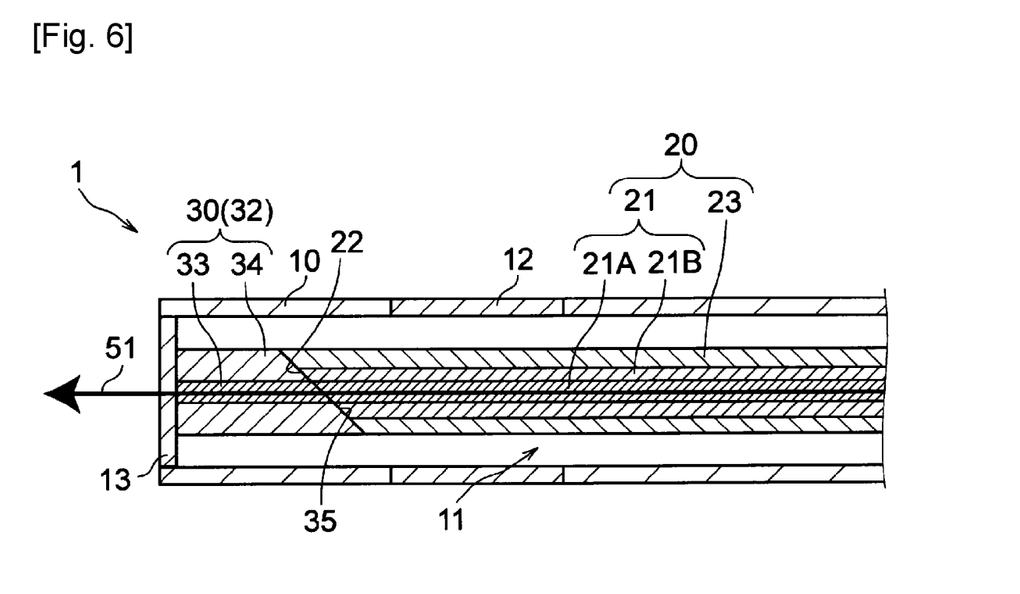
FIG. 6 shows a cross-sectional view of a modified example of the light therapy diagnostic device of FIG. 3.

FIGS. 5 and 6 show an example where the transparent member 30 is a short optical waveguide 32. As shown in FIG. 5, the transparent member 30 may be a short optical waveguide 32 having a shorter optical path than the optical waveguide 20. The short optical waveguide 32 may have a core 33 and a clad 34. Also by configuring the transparent member 30 in this manner, the emission direction of the first 51 can be easily switched. For example, as shown in FIG. 5, in the state where the optical waveguide 20 and the short optical waveguide 32 (in detail, the core 21 of the optical waveguide 20 and the core 33 of the short optical waveguide 32) are separated from each other, the first light 51 guided through the core 21 is reflected at the distal end part of the optical waveguide 20. Also, as shown in FIG. 6, in the state where the optical waveguide 20 and the short optical waveguide 32 are in contact with each other, the optical waveguide 20 and the short optical waveguide 32 function as one waveguide, and so it becomes possible to emit the first light 51 in the distal direction.

It is preferable that a normal of a proximal end surface 35 of the short optical waveguide 32 is inclined with respect to the longitudinal direction of the shaft 10. This makes it easier to bring the distal end surface 22 of the core 21 of the optical waveguide 20 into contact with the proximal end surface 35 of the short optical waveguide 32. As a result, it becomes easy to connect the optical waveguide 20 to the short optical waveguide 32, and the first light 51 is easily emitted in the distal direction.

In the state that the device 1 is viewed from the longitudinal direction of the shaft 10, it is preferable that the core 21 of the optical waveguide 20 and the core 33 of the short optical waveguide 32 are arranged so as to overlap with each other, and more preferably, the optical axis of the short optical waveguide 32 is arranged so as to overlap with the optical axis of the optical waveguide 20. Thereby, when the optical waveguide 20 is brought into contact with the short optical waveguide 32, the first light 51 can easily enter the short optical waveguide 32 from the optical waveguide 20.

As shown in FIGS. 2 to 6, the transparent member 30 is preferably disposed in contact with the distal emission window 13, but may be disposed adjacent to the distal emission window 13.

The configuration of the optical waveguide 20 is explained with reference to FIGS. 7 to 8. The optical waveguide 20 may have one or more single-core fibers in which one core is disposed in one clad, or may have one or more multi-core fibers in which a plurality of cores are disposed in one clad.

Figure 7:
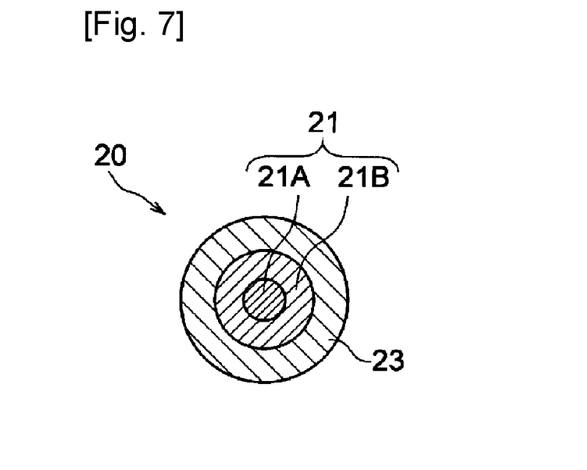
FIG. 7 shows a cross-sectional view taken along a line VII-VII of the light therapy diagnostic device show in FIG. 2.

As shown in FIG. 7, the optical waveguide 20 preferably includes a first core 21A, a second core 21B disposed outside the first core 21A, and a clad 23 disposed outside the second core 21B. Here, a refractive index n1 of the first core 21A, a refractive index n2 of the second core 21B, and a refractive index n3 of the clad 23 satisfy the relationship of n1>n2>n3. By disposing the second core 21B on an outer circumference of the first core 21A in this manner, the second light 52 can be easily emitted from the entire circumference of the shaft 10, so that it can be emitted over a wide range at once. The first core 21A, the second core 21B and the clad 23 are preferably arranged concentrically. As a result, the first light 51 can be guided by the first core 21A, and the second light 52 can be guided by the first core 21A and the second core 21B, while the clad 23 prevents the lights from leaking.

Figure 8:
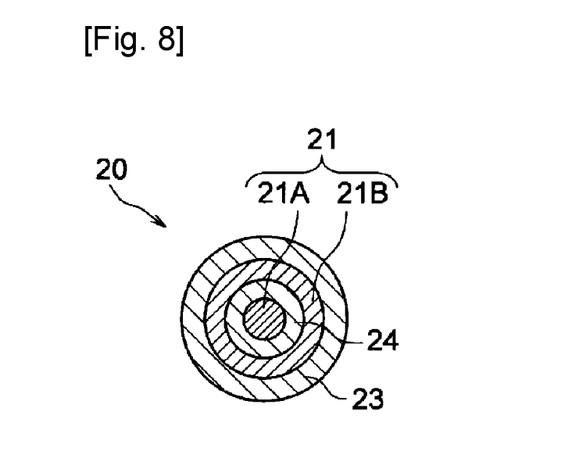
FIG. 8 shows a cross-sectional view of a modified example of the light therapy diagnostic device of FIG. 7.

FIG. 8 shows a cross-sectional view of a modified example of the optical waveguide 20 shown in FIG. 7. As shown in FIG. 8, the optical waveguide 20 preferably includes an intermediate clad 24 disposed outside the first core 21A and inside the second core 21B. Here, the refractive index n1 of the first core 21A, the refractive index n2 of the second core 21B, and a refractive index n4 of the intermediate clad 24 satisfy the relationship of n1>n2>n4. Thereby, the light guided by the first core 21A can be confined by the intermediate clad 24, and the light guided by the second core 21B can be confined by the intermediate clad 24 and the clad 23. As a result, leakage of the light from the optical waveguide 20 can be prevented. The refractive index n4 of the intermediate clad 24 may be the same as or different from the refractive index n3 of the clad 23.

Figure 9:
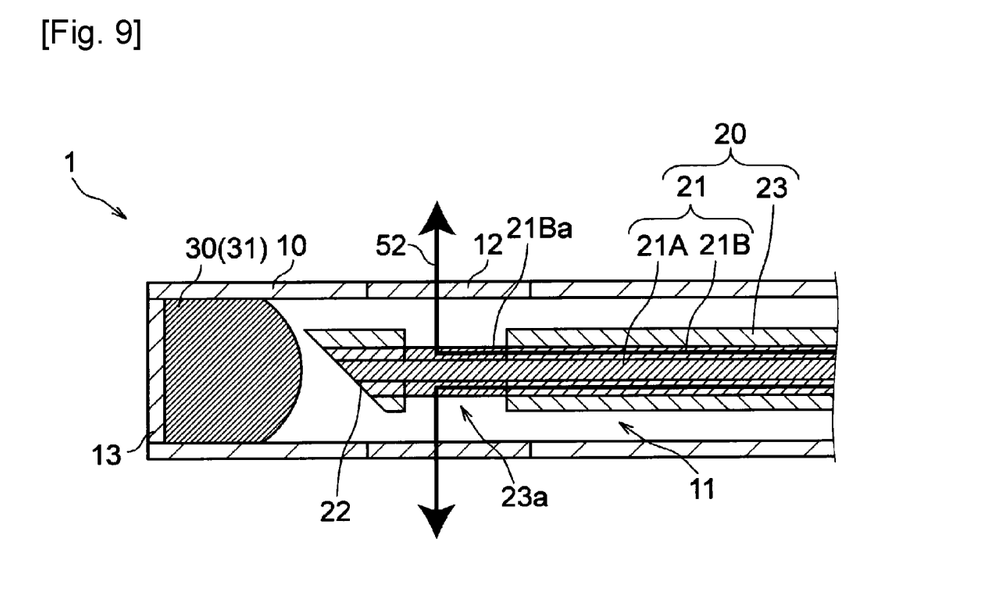
FIG. 9 shows a cross-sectional view of a modified example of the light therapy diagnostic device of FIG. 4.

FIG. 9 shows a cross-sectional view of a modified example of the device 1 of FIG. 4. As shown in FIG. 9, the lateral emission window 12 is preferably located at a position corresponding to a non-existing region 23a of the clad 23. Thereby, the first light 51 or the second light 52 guided by core 21 can be emitted toward the lateral direction from the non-existing region 23a of the clad 23. Specifically, it is preferable that the second light 52 is emitted toward the lateral direction from the non-existing region 23a of the clad 23. That the lateral emission window 12 is located at a position corresponding to the non-existing region 23a of the clad 23 means that the non-existing region 23a of the clad 23 and the lateral emission window 12 of the shaft 10 overlaps with each other at least in part when the optical waveguide 20 is located at a certain position of the shaft 10.

The non-existing region 23a of the clad 23 is a region in which the core 21 (the first core 21A or the second core 21B, preferably the second core 21B) inside the clad 23 is exposed to the outside due to the absence of the clad 23. Examples of a method of forming the non-existing region 23a of the clad 23 in this manner include a method of mechanically or chemically removing the clad 23, and for example, laser processing and etching processing are mentioned.

The non-existing region 23a of the clad 23 is preferably disposed so as to extend in the circumferential direction, and more preferably disposed over the entire circumference of the optical waveguide 20. Thereby, the second light 52 can be emitted over a wide area at once.

As shown in FIG. 9, the second core 21B preferably has a light diffusion region 21Ba proximal to the distal end surface 22 of the core 21. By providing the light diffusion region 21Ba in the second core 21B in this manner, the second light 52 can be suitably diffused, so that the second light 52 can be emitted over a wide range at once.

It is preferable that the surface roughness Ra of an outer surface of the second core 21B in the light diffusion region 21Ba is larger than the surface roughness Ra of an outer surface of the second core 21B in a distal region distal to the light diffusion region 21Ba. Here, the surface roughness Ra is determined based on an arithmetic average roughness Ra specified in JIS B 0601 (2001). By setting the surface roughness in this manner, the second light 52 can be efficiently diffused from the light diffusion region 21Ba, so that it can be emitted over a wide range at once.

Examples of a method of roughening the outer surface of the second core 21B in the light diffusion region 21Ba include a method of mechanically or chemically roughening the surfaces, and for example, etching, blasting, scribing, wire-brushing, a method of using sandpaper, and the like are mentioned.

It is preferable that the second core 21B contains light diffusing particles in the light diffusion region 21Ba. Thereby, the second light 52 can be efficiently diffused in the light diffusion region 21Ba, so that it can be emitted over a wide range at once. Examples of the light diffusing particles include inorganic particles such as titanium oxide, barium sulfate and calcium carbonate, and organic particles such as crosslinked acrylic particles and crosslinked styrene particles.

It is preferable that the length of the light diffusion region 21Ba of the second core 21B or the length of the non-existing region 23a of the clad 23 in the longitudinal direction of the shaft 10 is shorter than that of the lateral emission window 12. This makes it easier to emit the second light 52 toward the lateral direction of the shaft 10 without loss.

As shown in FIGS. 2 to 6, it is preferable that a distal end of the shaft 10 is closed. Thereby, liquids such as body fluids are prevented from entering the lumen 11 of the shaft 10. A normal of a distal end surface of the shaft 10 may be parallel to the optical axis of the optical waveguide 20.

Although it is not shown in the drawings, the shaft 10 may be composed of a plurality of members. For example, the shaft 10 may include a cylindrical shaft body having an opening at a distal end thereof, and a cap provided at a distal end part of the shaft body and closing the opening of the shaft body. In that case, the distal emission window 13 may be formed on the cap. Thereby, a part of the distal emission window 13 and the shaft 10, where the emission window is not formed, can be easily composed of a different material. Regarding a material constituting the cap, the description of the constituent material of the shaft 10 can be referred to.

Figure 10:
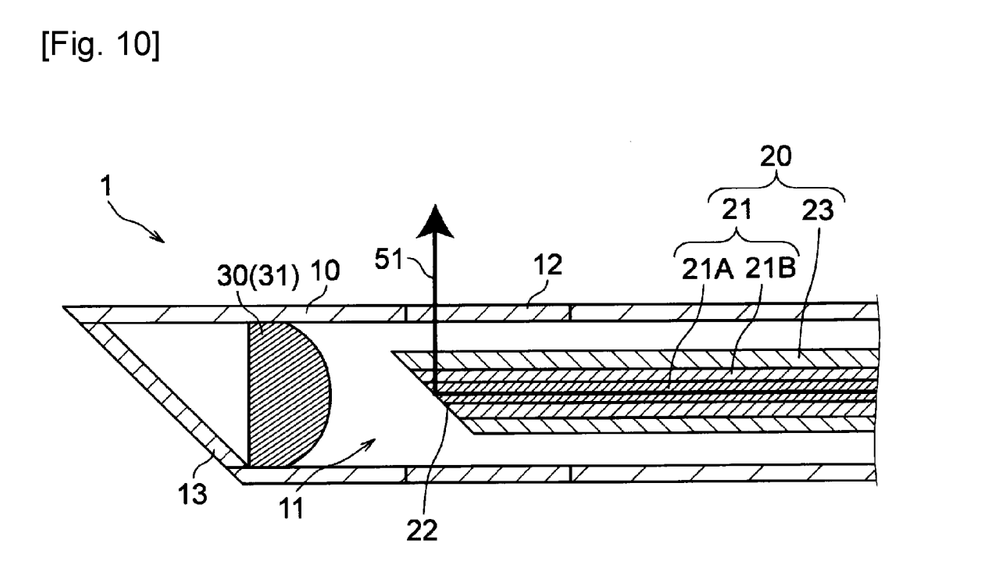
FIG. 10 shows a cross-sectional view of another modified example of the light therapy diagnostic device of FIG. 2.

FIG. 10 shows a cross-sectional view of a modified example of the device 1 of FIG. 2. As shown in FIG. 10, in a cross section along the longitudinal direction of the shaft 10, a distal end part of the shaft 10 may be formed in a sharp shape formed by one line or may be formed in a sharp shape formed by two or more lines. A distal end of the shaft 10 may be located at an outer end of the shaft 10 in a radial direction or may be located at a center of the longitudinal axis of the shaft 10. In this manner, it is preferable that the distal end part of the shaft 10 is sharpened. Since the distal end part of the shaft 10 can be punctured into a tissue, a position of the shaft 10 in a body can be fixed. As a result, it becomes easy to emit the first light 51 and the second light 52 for image diagnosis and treatment.

As shown in FIG. 1, a proximal part of the optical waveguide 20 is preferably connected to a circumferential rotating member 41 that rotates the optical waveguide 20 in the circumferential direction of the shaft 10. More preferably, the optical waveguide 20 rotates with respect to the shaft 10 around its optical axis. Since the optical waveguide 20 can be rotated around its optical axis, the emission position of the light from the lateral emission window 12 in the circumferential direction of the shaft 10 can be adjusted.

It is preferable that the proximal part of the optical waveguide 20 is connected to the circumferential rotating member 41, the circumferential rotating member 41 is configured to stop rotating at a predetermined rotation angle, and the distal end surface of the optical waveguide 20 (preferably the distal end surface 22 of the core 21) and the proximal end surface 35 of the short optical waveguide 32 come to be parallel to each other in the state where the circumferential rotating member is at the predetermined rotation angle. By rotating the circumferential rotating member 41, it is possible to switch between contact and non-contact between the optical waveguide 20 and the short optical waveguide 32. In addition, by forming the distal end surface of the optical waveguide 20 and the proximal end surface 35 of the short optical waveguide 32 parallel to each other, it becomes easy to bring the optical waveguide 20 into contact with the short optical waveguide 32.

Although it is not shown in the drawings, the shaft 10 may be provided with a balloon on a distal part thereof. In particular, the shaft 10 may include a balloon connected to the lumen thereof. The balloon may be located so as to cover the lateral emission window 12 or may be located distal to or proximal to the lateral emission window 12, in relation to the lateral emission window 12 provided on the shaft 10. Alternatively, the balloon may cover the distal emission window 13 or both the lateral emission window 12 and the distal emission window 13. It is preferable that the balloon is attached to the shaft 10 so that an attaching part of the balloon to the shaft 10 does not overlap with the lateral emission window 12 and the distal emission window 13. In the case where the light can pass through the balloon, the balloon may be attached to the shaft 10 so as to overlap with the lateral emission window 12. By providing the balloon on the shaft 10, the device 1 can be fixed in a body cavity, and the light can be stably emitted from the lateral emission window 12. In the case where the balloon is arranged on the shaft 10 so as to cover the lateral emission window 12, the balloon is preferably made of a highly transparent material to prevent attenuation of the light emitted from the lateral emission window 12.

Each of the above preferred embodiments can be combined as necessary to form a part of the configuration of the light therapy diagnostic device of the present invention.

The present invention also provides a method for operating the above light therapy diagnostic device 1. One embodiment of the method for operating the light therapy diagnostic device 1 of the present invention comprises steps of: guiding the first light 51 to the optical waveguide 20 in the state where the core 21 is in contact with the transparent member 30; guiding the first light 51 to the optical waveguide 20 in the state where the core 21 is apart from the transparent member 30; and guiding the second light 52 to the optical waveguide 20 to emit the second light 52 from the lateral emission window 12.

The first light 51 is guided to the optical waveguide 20 in the state where the core 21 is in contact with the transparent member 30. Thereby, the first light 51 can be emitted from the distal emission window 13 toward a distal direction, and therefore, a condition of a living tissue located on a distal side of the device 1 can be grasped.

The first light 51 is guided to the optical waveguide 20 in the state where the core 21 is apart from the transparent member 30. Thereby, the first light 51 can be emitted from the lateral emission window 12 toward a lateral direction, and therefore, a condition of a living tissue located on a lateral side of the device 1 can be grasped.

The second light 52 is guided to the optical waveguide 20 and the second light 52 is emitted from the lateral emission window 12. Thereby, the second light 52 can be emitted to a tissue located on a lateral side of the shaft 10, and therefore, treatment of living using the light can be conducted.

This application claims priority to Japanese Patent Application No. 2019-109903, filed on Jun. 12, 2019. All of the contents of the Japanese Patent Application No. 2019-109903, filed on Jun. 12, 2019, are incorporated by reference herein.

REFERENCE SIGNS LIST

1: light therapy diagnostic device
10: catheter shaft
11: lumen
12: lateral emission window
13: distal emission window
20: optical waveguide
21: core
21A: first core
21B: second core
21Ba: light diffusion region
22: distal end surface of core
23: clad
23a: non-existent region of clad
24: intermediate clad
30: transparent member
31: resin lump
32: short optical waveguide
33: core of short optical waveguide
34: clad of short optical waveguide
35: proximal end surface of short optical waveguide
40: handle
41: circumferential rotating member
42: light source
51: first light
52: second light

The invention claimed is:
1. A light therapy diagnostic device comprising:
 a shaft having a distal end and a proximal end in a longitudinal direction and a lumen extending in the longitudinal direction;
 an optical waveguide disposed in the lumen of the shaft such that the optical waveguide is movable forward and backward in the longitudinal direction; and
 a transparent member disposed in the lumen of the shaft and located distal to the optical waveguide, wherein:
 the optical waveguide guides a first light and a second light;
 the shaft has a lateral emission window located on a lateral part of the shaft and a distal emission window located on a distal end part of the shaft;
 the lateral emission window is configured to allow the first light and the second light to be emitted from the optical waveguide toward a lateral direction, which is perpendicular to the longitudinal direction;

the distal emission window is configured to allow the first light to be emitted from the optical waveguide toward a distal direction, which is parallel to the longitudinal direction;

the optical waveguide comprises a core and a clad, wherein a distal end surface of the core is inclined with respect to an optical axis of the optical waveguide; and the light therapy diagnostic device provides a forward observation mode in which the first light passes through the transparent member toward the distal direction in a state where the optical waveguide is in contact with the transparent member, and a lateral observation mode in which the first light guided through the core is reflected toward the lateral direction at a distal end part of the optical waveguide in a state where the optical waveguide is apart from the transparent member; and the shaft and the optical waveguide are configured such that the forward observation mode and the lateral observation mode are switched by moving the optical waveguide forward or backward in the lumen of the shaft while keeping the optical waveguide remaining in the shaft, without withdrawing the optical waveguide from the shaft.

2. The light therapy diagnostic device according to claim 1, wherein the transparent member is a short optical waveguide having a shorter optical path than the optical waveguide, and a proximal end surface of the short optical waveguide is inclined with respect to the longitudinal direction of the shaft.

3. The light therapy diagnostic device according to claim 2, further comprising a circumferential rotating member, to which a proximal part of the optical waveguide is connected, that is configured to stop rotating at a predetermined rotation angle, wherein the optical waveguide and the short optical waveguide are configured such that a distal end surface of the optical waveguide and a proximal end surface of the short optical waveguide are parallel to each other in a state where the circumferential rotation member is at the predetermined rotation angle.

4. The light therapy diagnostic device according to claim 1, wherein the transparent member is made of a material softer than the optical waveguide.

5. The light therapy diagnostic device according to claim 1, wherein a distal end surface of the transparent member is perpendicular to the longitudinal direction of the shaft.

6. The light therapy diagnostic device according to claim 1, wherein the lateral emission window is disposed over an entire circumference of the shaft.

7. The light therapy diagnostic device according to claim 1, further comprising a circumferential rotating member, wherein the circumferential rotating member is connected to a proximal part of the optical waveguide such that the optical waveguide is rotatable by rotating the circumferential rotating member in a circumferential direction of the shaft.

8. The light therapy diagnostic device according to claim 1, wherein the core of the optical waveguide comprises a first core, a second core disposed on the first core, and the clad disposed on the second core, and a refractive index n1 of the first core, a refractive index n2 of the second core, and a refractive index n3 of the clad satisfy the relationship of n1>n2>n3.

9. The light therapy diagnostic device according to claim 8, wherein the optical waveguide further comprises an intermediate clad disposed between the first core and the second core, and the refractive index n1 of the first core, the refractive index n2 of the second core, and a refractive index n4 of the intermediate clad satisfy the relationship of n1>n2>n4.

10. The light therapy diagnostic device according to claim 8, wherein the optical waveguide has a non-existent area of the clad where the clad does not exist on the second core, and the lateral emission window is located at a position corresponding to the non-existent area of the clad such that the second light is allowed to be emitted from the optical waveguide toward the lateral direction through the lateral emission window.

11. The light therapy diagnostic device according to claim 8, wherein the second core has a light diffusion region disposed proximal to the distal end surface of the core such that the second light is allowed to be emitted toward the lateral direction.

12. The light therapy diagnostic device according to claim 11, wherein the second core contains light diffusing particles in the light diffusion region.

13. The light therapy diagnostic device according to claim 1, wherein a distal end part of the shaft is tapered.

14. The light therapy diagnostic device according to claim 1, further comprising a light source that generates the first light; and a lens disposed between the light source and a distal end surface of the core, wherein the light source, the lens and the optical waveguide are configured such that the first light is guided through the optical waveguide.

15. The light therapy diagnostic device according to claim 1, further comprising a balloon, wherein the balloon is connected to the lumen of the shaft.

16. A method for operating the light therapy diagnostic device according to claim 1, comprising the steps of:

guiding the first light to the optical waveguide in the forward observation mode to emit the first light from the distal emission window toward the distal direction;

moving the optical waveguide in the lumen of the shaft in the longitudinal direction to switch the forward observation mode to the lateral observation mode while keeping the optical waveguide remaining in the shaft, without withdrawing the optical waveguide from the shaft;

guiding the first light to the optical waveguide in the lateral observation mode to emit the first light from the lateral emission window toward the lateral direction; and guiding the second light to the optical waveguide to emit the second light from the lateral emission window in a state where the optical waveguide is apart from the transparent member.

17. The light therapy diagnostic device according to claim 1, further comprising at least one light source for generating the first light and the second light, wherein the light source and the optical waveguide are configured such that the first and second lights are guided through the optical waveguide, and a wavelength of the second light is different from a wavelength of the first light.

18. The light therapy diagnostic device according to claim 1, wherein the first light is an observation light and the second light is a treatment light.

19. The light therapy diagnostic device according to claim 1, wherein the light therapy diagnostic device is a device used for a photodynamic therapy or a photo-immunotherapy.

20. The light therapy diagnostic device according to claim 1, wherein a distal end surface of the shaft is a flat surface perpendicular to the longitudinal direction or a curved surface.

21. The light therapy diagnostic device according to claim 1, wherein the distal end surface of the core is a flat surface, and an inclination angle of normal of the distal end surface of the core with respect to the optical axis of the optical waveguide is 40 degrees or larger and 47 degrees or smaller.

22. The light therapy diagnostic device according to claim 1, wherein refractive indexes of the core of the optical waveguide and the transparent member are the same value.

* * * * *